US 7,654,958 B2

(12) United States Patent
Byrd et al.

(10) Patent No.: US 7,654,958 B2
(45) Date of Patent: Feb. 2, 2010

(54) METHOD AND APPARATUS FOR ULTRASOUND IMAGING WITH AUTOFREQUENCY SELECTION

(75) Inventors: Charles Bryan Byrd, Medford, NJ (US); Praveen Dala-Krishna, Bensalem, PA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1143 days.

(21) Appl. No.: 10/827,520

(22) Filed: Apr. 20, 2004

(65) Prior Publication Data

US 2005/0240103 A1 Oct. 27, 2005

(51) Int. Cl.
*A61B 8/00* (2006.01)
*A61B 8/12* (2006.01)
*A61B 8/14* (2006.01)

(52) U.S. Cl. .................. 600/443; 600/437; 600/442; 600/459; 382/148; 382/299; 73/602

(58) Field of Classification Search ............... 600/437, 600/442; 382/148, 299; 73/602
See application file for complete search history.

(56) References Cited

U.S. PATENT DOCUMENTS

| 4,161,121 A | 7/1979 | Zitelli et al. |
| 4,241,610 A | 12/1980 | Anderson |
| 4,442,713 A * | 4/1984 | Wilson et al. ................. 73/599 |
| 4,462,408 A | 7/1984 | Silverstein et al. |
| 4,519,260 A | 5/1985 | Fu et al. |
| 4,534,221 A * | 8/1985 | Fife et al. ..................... 73/626 |
| 4,576,177 A | 3/1986 | Webster, Jr. |
| 4,605,009 A | 8/1986 | Pourcelot et al. |
| 4,841,977 A | 6/1989 | Griffith et al. |
| 4,890,268 A | 12/1989 | Smith et al. |
| 4,917,097 A | 4/1990 | Proudian et al. |
| 4,951,677 A | 8/1990 | Crowley et al. |
| 5,002,059 A | 3/1991 | Crowley et al. |
| 5,090,956 A | 2/1992 | McCoy |
| 5,105,819 A | 4/1992 | Wollschlager et al. |
| 5,152,294 A | 10/1992 | Mochizuki et al. |
| 5,158,087 A | 10/1992 | Gatzke |
| 5,170,793 A | 12/1992 | Takano et al. |
| 5,195,968 A | 3/1993 | Lundquist et al. |
| 5,254,088 A | 10/1993 | Lundquist et al. |

(Continued)

OTHER PUBLICATIONS

Keith S. Dickerson et al., "Comparison of Conventional and Transverse Doppler Sonograms", J. Ultrasound Med., 1993, pp. 497-506, vol. 12.

(Continued)

*Primary Examiner*—Brian Casler
*Assistant Examiner*—James Kish
(74) *Attorney, Agent, or Firm*—The Marbury Law Group, PLLC

(57) ABSTRACT

An ultrasound imaging system is provided with an interface for receiving user input, and a controller coupled to the interface, the controller being adapted and configured to adjust parameters for a catheter-based ultrasound probe in response to received user input. Preferably, the controller is programmed to receive a user request for a desired imaging depth, determine an imaging frequency that corresponds to the desired imaging depth, and adjust the imaging frequency of the system to the determined imaging frequency that corresponds to the desired imaging depth.

22 Claims, 5 Drawing Sheets

U.S. PATENT DOCUMENTS

| | | | |
|---|---|---|---|
| 5,279,559 A | | 1/1994 | Barr |
| 5,301,674 A | * | 4/1994 | Erikson et al. ............. 600/447 |
| 5,307,816 A | | 5/1994 | Hashimoto et al. |
| 5,309,914 A | | 5/1994 | Iinuma |
| 5,325,860 A | | 7/1994 | Seward et al. |
| 5,336,182 A | | 8/1994 | Lundquist et al. |
| 5,345,938 A | | 9/1994 | Nishiki et al. |
| 5,345,940 A | | 9/1994 | Seward et al. |
| 5,357,550 A | | 10/1994 | Asahina et al. |
| 5,358,478 A | | 10/1994 | Thompson et al. |
| 5,361,767 A | * | 11/1994 | Yukov ..................... 600/442 |
| 5,364,351 A | | 11/1994 | Heinzelman et al. |
| 5,372,138 A | | 12/1994 | Crowley et al. |
| 5,385,148 A | | 1/1995 | Lesh et al. |
| 5,395,327 A | | 3/1995 | Lundquist et al. |
| 5,438,997 A | | 8/1995 | Sieben et al. |
| 5,456,258 A | | 10/1995 | Kondo et al. |
| 5,456,664 A | | 10/1995 | Heinzelman et al. |
| 5,470,350 A | | 11/1995 | Buchholtz et al. |
| 5,499,630 A | | 3/1996 | Hiki et al. |
| 5,515,853 A | | 5/1996 | Smith et al. |
| 5,515,856 A | | 5/1996 | Olstad et al. |
| 5,531,686 A | | 7/1996 | Lundquist et al. |
| 5,560,362 A | | 10/1996 | Sliwa, Jr. et al. |
| 5,588,432 A | | 12/1996 | Crowley |
| 5,622,174 A | | 4/1997 | Yamazaki |
| 5,662,116 A | | 9/1997 | Kondo et al. |
| 5,697,965 A | | 12/1997 | Griffin, III |
| 5,699,805 A | | 12/1997 | Seward et al. |
| 5,701,897 A | | 12/1997 | Sano |
| 5,704,361 A | | 1/1998 | Seward et al. |
| 5,713,363 A | | 2/1998 | Seward et al. |
| 5,715,817 A | | 2/1998 | Stevens-Wright et al. |
| 5,722,403 A | | 3/1998 | McGee et al. |
| 5,749,364 A | | 5/1998 | Sliwa, Jr. et al. |
| 5,788,636 A | | 8/1998 | Curley |
| 5,795,299 A | | 8/1998 | Eaton et al. |
| 5,797,848 A | | 8/1998 | Marian et al. |
| 5,800,356 A | | 9/1998 | Criton et al. |
| 5,807,324 A | | 9/1998 | Griffin, III |
| 5,846,205 A | | 12/1998 | Curley et al. |
| 5,888,577 A | | 3/1999 | Griffin, III et al. |
| 5,891,088 A | | 4/1999 | Thompson et al. |
| 5,906,579 A | | 5/1999 | Vander Salm et al. |
| 5,916,168 A | | 6/1999 | Pedersen et al. |
| 5,921,978 A | | 7/1999 | Thompson et al. |
| 5,928,276 A | | 7/1999 | Griffin, III et al. |
| 5,931,863 A | | 8/1999 | Griffin, III et al. |
| 5,935,102 A | | 8/1999 | Bowden et al. |
| 5,938,616 A | | 8/1999 | Eaton et al. |
| 5,954,654 A | | 9/1999 | Eaton et al. |
| 6,013,072 A | | 1/2000 | Winston et al. |
| 6,033,378 A | | 3/2000 | Lundquist et al. |
| 6,039,693 A | | 3/2000 | Seward et al. |
| 6,085,117 A | | 7/2000 | Griffin, III et al. |
| 6,095,976 A | * | 8/2000 | Nachtomy et al. .......... 600/443 |
| 6,144,870 A | | 11/2000 | Griffin, III |
| 6,171,248 B1 | | 1/2001 | Hossack et al. |
| 6,173,205 B1 | | 1/2001 | Griffin, III et al. |
| 6,190,353 B1 | | 2/2001 | Makower et al. |
| 6,210,333 B1 | | 4/2001 | Gardner et al. |
| 6,224,556 B1 | | 5/2001 | Schwartz et al. |
| 6,228,028 B1 | | 5/2001 | Klein et al. |
| 6,228,032 B1 | | 5/2001 | Eaton et al. |
| 6,261,246 B1 | | 7/2001 | Pantages et al. |
| 6,293,943 B1 | | 9/2001 | Panescu et al. |
| 6,306,096 B1 | | 10/2001 | Seward et al. |
| 6,306,097 B1 | | 10/2001 | Park et al. |
| 6,310,828 B1 | | 10/2001 | Mumm et al. |
| 6,322,507 B1 | * | 11/2001 | Passi et al. ................. 600/437 |
| 6,358,208 B1 | * | 3/2002 | Lang et al. ................. 600/438 |
| 6,360,027 B1 | | 3/2002 | Hossack et al. |
| 6,368,275 B1 | | 4/2002 | Sliwa et al. |
| 6,385,489 B1 | | 5/2002 | Griffin, III et al. |
| 6,398,731 B1 | | 6/2002 | Mumm et al. |
| 6,423,002 B1 | | 7/2002 | Hossack |
| 6,440,488 B2 | | 8/2002 | Griffin, III et al. |
| 6,443,894 B1 | | 9/2002 | Sumanaweera et al. |
| 6,475,148 B1 | | 11/2002 | Jackson et al. |
| 6,475,149 B1 | | 11/2002 | Sumanaweera |
| 6,482,161 B1 | | 11/2002 | Sumanaweera et al. |
| 6,485,455 B1 | | 11/2002 | Thompson et al. |
| 6,491,633 B1 | | 12/2002 | Krishnan et al. |
| 6,503,202 B1 | | 1/2003 | Hossack et al. |
| 6,517,488 B1 | | 2/2003 | Hossack |
| 6,527,717 B1 | | 3/2003 | Jackson et al. |
| 6,532,378 B2 | | 3/2003 | Saksena et al. |
| 6,554,770 B1 | | 4/2003 | Sumanaweera et al. |
| 6,589,182 B1 | | 7/2003 | Loftman et al. |
| 6,605,043 B1 | | 8/2003 | Dreschel et al. |
| 6,607,488 B1 | | 8/2003 | Jackson et al. |
| 6,607,528 B1 | | 8/2003 | Quick et al. |
| 6,612,992 B1 | | 9/2003 | Hossack et al. |
| 6,645,147 B1 | | 11/2003 | Jackson et al. |
| 6,648,875 B2 | | 11/2003 | Simpson et al. |
| 6,709,396 B2 | | 3/2004 | Flesch et al. |
| 6,908,434 B1 | | 6/2005 | Jenkins et al. |
| 6,923,768 B2 | | 8/2005 | Camus et al. |
| 7,396,332 B2 | * | 7/2008 | Taimisto et al. ............. 600/467 |
| 2001/0020126 A1 | * | 9/2001 | Swanson et al. ............ 600/407 |
| 2003/0045162 A1 | | 3/2003 | Friedman |
| 2003/0158483 A1 | | 8/2003 | Jackson et al. |
| 2004/0039286 A1 | * | 2/2004 | Kuban et al. ................ 600/467 |
| 2004/0097805 A1 | | 5/2004 | Verard et al. |
| 2004/0249282 A1 | | 12/2004 | Olslad |
| 2005/0203390 A1 | | 9/2005 | Torp et al. |

OTHER PUBLICATIONS

David J. Sahn, "Phased Arrays for Multiplane Esophageal Echos in Infants", Summary Statement, Diagnostic Radiology Study Section, Jun. 1990.

David J. Sahn, "Instrumentation and Physical Factors Related to Visualization of Stenotic and Regurgitant Jets by Doppler Color Flow Mapping", JACC, Nov. 1988, pp. 1354-1365, vol. 12, No. 5.

David J. Sahn, "Advances in Ultrasound Imaging for Congenital Heart Disease Diagnosis and Management", Pediatric Cardiology, Nov. 26-Dec. 1, 1989, Proceedings of the III World Congress of Pediatric Cardiology, Bangkok.

David J. Sahn et al., "Important Roles of Transeophageal Color Doppler Flow Mapping Studies(TEE) in Infants with Congenital Heart Disease", Supplement to Journal of the American College of Cardiology, Feb. 1990, vol. 15, No. 2 (Supplement A).

David J. Sahn, "Applications of Color Flow Mapping in Pediatric Cardiology", Cardiology Clinics, May 1989, pp. 255-264, vol. 7, No. 2.

David J. Sahn et al., "Miniaturized High Frequency Phased Array Devices for High Resolution Neonatal and Intraoperative Imaging", Supplement to Journal of the American College of Cardiology, Feb. 1990, vol. 15, No. 2 (Supplement A).

Piero Tortoli et al., "Velocity Magnitude Estimation with Linear Arrays Using Doppler Bandwidth", Ultrasounics, 2001, pp. 157-161, vol. 39.

Lilliam M. Valdes-Cruz et al., "Transvascular Intracardiac Applications of a Miniaturized Phase-Array Ultrasonic Endoscope", Brief Rapid Communication, Mar. 1991, pp. 1023-1027, vol. 83, No. 3.

Lilliam M. Valdes-Cruz at al., "Experimental Animal Investigations of the Potential for New Approaches to Diagnostic Cardiac Imaging in Infants and Small Premature Infants from Intracardiac and Trasesophageal Approaches Using a 20MHz Real Time Ultrasound Imaging Catheter", Supplement to Journal of the American College of Cardiology, Feb. 1989, vol. 13, No. 2 (Supplement A).

P.N.T. Wells, "Velocity, Absorption and Attenuation in Biological Materials", Biomedical Ultrasonics, 1977, pp. 110-144.

Antonio L. Bartorelli, M.D. et al., "Plaque Characterization of Atherosclerotic Coronary Arteries by Intravascular Ultrasound", Echocardiography: A Journal of CV Ultrasound & Allied Tech, 1990, pp. 389-395, vol. 7, No. 4.

N. Bom et al., "Early and recent intraluminal ultrasound devices", International Journal of Cardiac Imaging, 1989, pp. 79-88, vol. 4.

R.J. Crowley et al., "Optimized ultrasound imaging catheters for use in the vascular system", International Journal of Cardiac Imaging, 1989, pp. 145-151, vol. 4.

R.J. Crowley, et al., "Ultrasound guided therapeutic catheters: recent developments and clinical results", International Journal of Cardiac Imaging, 1991, pp. 145-156, vol. 6.

Richard A. Carleton, M.D., et al., "Measurement of Left Ventricular Diameter In the Dog by Cardiac Catheterization", Circulation Research, May 1968, pp. 545-558, vol. XXII.

Taher Elkadi et al., "Importance of Color Flow Doppler (CFD) Imaging of the Right Ventricular Outflow Tract and Pulmonary Arteries by Transesophageal Echocardiography (TEE) During Surgery for CHD", Supplement III Circulation, Oct. 1990, p. III-438, vol. 82, No. 4.

Philip C. Currie, "Transeosphageal Echocardiography New Window to the Hearth", Circulation, Jul. 1989, pp. 215-217, vol. 88, No. 1.

Steven Schwartz et al., "In Vivo Intracardiac 2-D Echocardiography: Effects of Transducer Frequency, Imaging Approached and Comparison with Fiberoptic Angioscopy", JACC, Feb. 1990, pp. 29A, vol. 15, No. 2.

J. Souquet et al., "Transesophageal Phased Array for Imaging the Heart", IEEE Transactions on Biomedical Engineering, Oct. 1982, pp. 707-712, vol. BME-29, No. 10.

Craig J. Hartley, "Review of Intracoronary Doppler catheters", International Journal of Cardiac Imaging, 1989, pp. 159-168, vol. 4.

John McB. Hodgson et al., "Percutaneous Intravascular Ultrasound Imaging: Validation of a Real-Time Synthetic Aperture Array Catheter", American Journal of Cardiac Imaging, Mar. 1991, pp. 56-71, vol. 5, No. 1.

J. McB. Hodgson et al., "Clinical percutaneous imaging of corconary anatomy using an over-the-wire ultrasound catheter system", International Journal of Cardiact Imaging, 1989, pp. 187-193, vol. 4.

Brenda S. Kusay et al., "Realtime in Vivo Intracardiac Two-Dimensional Echocardiography and Color Flow Imaging: Approaches, Imaging Planes, and Echo Anatomy", Abstracts of the 62nd Scientific Sessions, 1989, p. II-581.

Charles T. Lancee, "A Transesophageal Phased Array Transducer for Ultrasonic Imaging of the Heart", 1987.

Natesa Pandian et al., "Enhanced Depth of Field in Intracardiac 2-D Echocardiography with a New Prototype, Low Frequency (12 MHz, 9 French) Ultrasound Catheter", Supplemental III Circulation, Oct. 1990, p. III-442, vol. 82, No. 4.

Natesa G. Pandian, M.D. et al., "Intravascular and Intracardiac Ultrasound Imaging: Current Research and Future Directions", Echocardiography: A Journal of CV Ultrasound & Allied Tech., 1990, pp. 377-387, vol. 7, No. 4.

Natesa G. Pandian, M.D. et al., "Intracardiac, Intravascular, Two-Dimensional, High-Frequency Ultrasound Imaging of Pulmonary Artery and Its Branches in Humans and Animals", Circulation, Jun. 1990, pp. 2007-2012, vol. 81, No. 6.

F. Ricou et al., "Applications of intravascular scanning and transesophageal echocardiography in congenital heart disease: tradeoffs and the merging of technologies", International Journal of Cardiac Imaging, 1991, pp. 221-230, vol. 6.

Samuel B. Ritter, M.D., et al., "Transesophageal real time Doppler flow imaging in congenital heart disease: experience with a new pediatric trasducer probe", 1989, Dynamedia, Inc.

Samuel B. Ritter, M.D., et al., "Pediatric Transesophageal Color Flow Imaging: Smaller Probes for Smaller Hearts", 1989.

David J. Sahn, M.D., et al., "Important Roles of Transesophageal Color Doppler Flow Mapping Studies (TEE) in Infants With Congenital Heart Disease", IACC, Feb. 1990, p. 204A, vol. 15, No. 2.

David J. Sahn, M.D. et al., "Miniaturized High Frequency Phased Array Devices for High Resolution Neonatal and Intraoperative Imaging", JACC, Feb. 1990, p. 10A, vol. 15, No. 2.

David J. Sahn, M.D., et al., "Phased Arrays for Multiplane Esophageal Echos in Infants", Grant Application, Department of Health and Human Services Public Health Service, 1992.

Steven Schwartz, M.D., et al., "Intracardiac Echocardioraphic Guidance and Monitoring During Aortic and Mitral Balloon Valvuloplasty", JACC, Feb. 1990, p. 104A, vol. 15, No. 2.

James B. Seward, M.D. et al., "Biplanar Transesophageal Echocardiography: Anatomic Correlations, Image Orientation, and Clinical Applications", Mayo Clin Proc., 1990, pp. 1198-1213, vol. 65.

James B. Seward, M.D. et al., "Wide-Field Transesophageal Echocardiographic Tomography: Feasibility Study", Mayo Clin Proc. 1990, pp. 31-37, vol. 65.

Khalid H. Sheikh, M.D., et al., "Interventional Applications of Intravascular Ultrasound Imaging: Initial Experience and Future Perspectives", Echocadiography: A Journal of CV Ultrasound & Allied Tech., pp. 433-441, vol. 7, No. 4.

Paul G. Yock, M.D., et al., "Two-Dimensional Intravascular Ultrasound: Technical Development and Initial Clinical Experience", Journal of American Society of Echocardiography, 1989, pp. 296-304, vol. 2, No. 4.

Paul G. Yock, M.D. et al., "Real-Time, Two-Dimensional Catheter Ultrasound: A New Technique for High-Resolution Intravascular Imaging", JACC, Feb. 1988, p. 130A, vol. 11, No. 2.

P. Yock et al., "Intravascular Two-Dimensional Catheter Ultrasound: Initial Clinical Studies", Abstracts of the 61st Scientist Sessions, p. II-21.

Michael J. Eberle et al., "Validation of a New Real Time Percotaneous Intravascular Ultrasound Imaging Catheter", Abstracts of the 61st Scientist Sessions, p. II-21.

Natasa Pandian et al., "Intralurolonal Ultrasound Angloscopic Detection of Arterial Dissection and Intimal Flaps: In Vitro and In Vivo Studies", Abstracts of the 61st Scientist Sessions, p. II-21.

John A. Mallery et al., "Evaluation of an Intravascular ultrasound Imaging Catheter in Porcine Peripheral and Coronary Arteries In Vivo", Abstracts of the 61st Scientist Sessions, p. II-21.

Andrew Wintraub, M.D., "Realtime Intracardiac Two-Dimensional Echocardiography in the Catheterization Laboratory in Humans", Intravascular Imaging I, Mar. 19, 1990.

* cited by examiner

METHOD AND APPARATUS FOR ULTRASOUND IMAGING WITH AUTOFREQUENCY SELECTION

BACKGROUND OF THE INVENTION

1. Field of the Invention

The present invention is directed at medical imaging technology, and more particularly to a method and apparatus for ultrasound imaging with autofrequency selection.

2. Description of the Related Art

Medical imaging technology is used to improve the diagnosis and treatment of medical conditions. Presently available medical imaging technology includes a wide variety of ultrasound, X-ray, nuclear, magnetic resonance imaging (MRI) and other imaging systems.

In these medical imaging technologies, various parameters may be controlled that affect the resultant image. By way of example, with catheter-based ultrasound imaging technology, the imaging beam aperture size, imaging beam frequency, and apodization parameters may be adjusted as described in U.S. Pat. No. 6,629,929 to Jago ("Jago" hereafter) and U.S. Pat. No. 6,354,997 to Holley ("Holley" hereafter), which are incorporated by reference herein in their entirety. Other adjustable parameters for ultrasound and non-ultrasound imaging technologies also exist.

To adjust a parameter in a typical catheter-based ultrasound imaging system, a user inputs a desired parameter change, which is then implemented by the particular imaging system. This requires the user to know how the parameter change will affect the image, and may require the user to iteratively try a number of different parameter changes to achieve a desired result. Thus, this process may be tedious, time consuming, and involve significant user-system interaction.

Other problems with the prior art not described above can also be overcome using the teachings of the present invention, as would be readily apparent to one of ordinary skill in the art after reading this disclosure.

SUMMARY OF THE INVENTION

An ultrasound imaging system includes an interface for receiving user input and a controller coupled to the interface, the controller being adapted and configured to adjust parameters for a catheter-based ultrasound probe in response to received user input. User input may be in the form of a desired imaging depth or user designation of a feature within an image, such as by means of a touch screen. The controller is programmed to receive a user request for a desired imaging depth, automatically determine an imaging frequency that corresponds to the desired imaging depth, and adjust the imaging frequency of the catheter-based ultrasound probe to the determined imaging frequency that corresponds to the desired imaging depth. The controller may be further programmed so the imaging frequency is selected from a range of incremented frequencies separated by increments of about 0.1 MHz to about 0.5 MHz within a range of about 2 MHz to about 20 MHz. The controller may be further programmed so the imaging frequency is set to scan through a range of frequencies. The controller may be further programmed to receive an ultrasound image from the catheter-based ultrasound probe, determine a signal attenuation in the received ultrasound image at the determined imaging frequency, determine an imaging frequency that corresponds to the determined signal attenuation, and adjust the imaging frequency of the catheter-based ultrasound probe to the determined imaging frequency that corresponds to the determined signal attenuation. The controller may be further programmed to compare the determined signal attenuation to a predicted signal attenuation, and adjust the imaging frequency to the determined imaging frequency that corresponds to the determined signal attenuation if the determined signal attenuation diverges from the predicted signal attenuation by at least a known value. The controller may be further programmed to process a first image of a feature of interest imaged at the determined imaging frequency, adjust the imaging frequency of the catheter-based ultrasound probe by a delta-frequency, process a second image of the feature of interest imaged at the delta-frequency adjusted imaging frequency, compare a resolution of the first image to a resolution of the second image, and adjust the imaging frequency to the determined imaging frequency if the resolution of the first image is better than the resolution of the second image.

A method of controlling an ultrasound imaging system includes receiving a user request for a desired imaging depth or change in the present imaging depth, automatically determining an imaging frequency that corresponds to the desired imaging depth, and adjusting the imaging frequency of a catheter-based ultrasound probe to the determined imaging frequency that corresponds to the desired imaging depth. The desired imaging depth may be received as a user request for a scan through a range of frequencies to identify features at various depths. The desired imaging depth may be received as a user designation of a feature within an image, and determining the imaging frequency involves determining an imaging frequency that corresponds to the user designated feature. The imaging frequency may be selected from a range of incremented frequencies separated by increments of about 0.1 MHz to about 0.5 MHz within a range of about 2 MHz to about 20 MHz. The imaging frequency selection may be conducted as a scan through the range of frequencies. The method may include receiving an ultrasound image from the catheter-based ultrasound probe, determining a signal attenuation in the received ultrasound image at the determined imaging frequency, determining an imaging frequency that corresponds to the determined signal attenuation, and adjusting the imaging frequency of the catheter-based ultrasound probe to the determined imaging frequency that corresponds to the determined signal attenuation. The method may further include comparing the determined signal attenuation to a predicted signal attenuation, and adjusting the imaging frequency to the determined imaging frequency that corresponds to the determined signal attenuation if the determined signal attenuation diverges from the predicted signal attenuation by at least a known value. The method may further include processing a first image of a feature of interest imaged at the determined imaging frequency, adjusting the imaging frequency of the catheter-based ultrasound probe by a delta-frequency, processing a second image of the feature of interest imaged at the delta-frequency adjusted imaging frequency, comparing a resolution of the first image to a resolution of the second image, and adjusting the imaging frequency to the determined imaging frequency if the resolution of the first image is better than the resolution of the second image.

DETAILED DESCRIPTION OF THE EXEMPLARY EMBODIMENTS

Reference will now be made in detail to exemplary embodiments of the present invention. Wherever possible, the same reference numbers will be used throughout the drawings to refer to the same or like parts.

Figure 5:
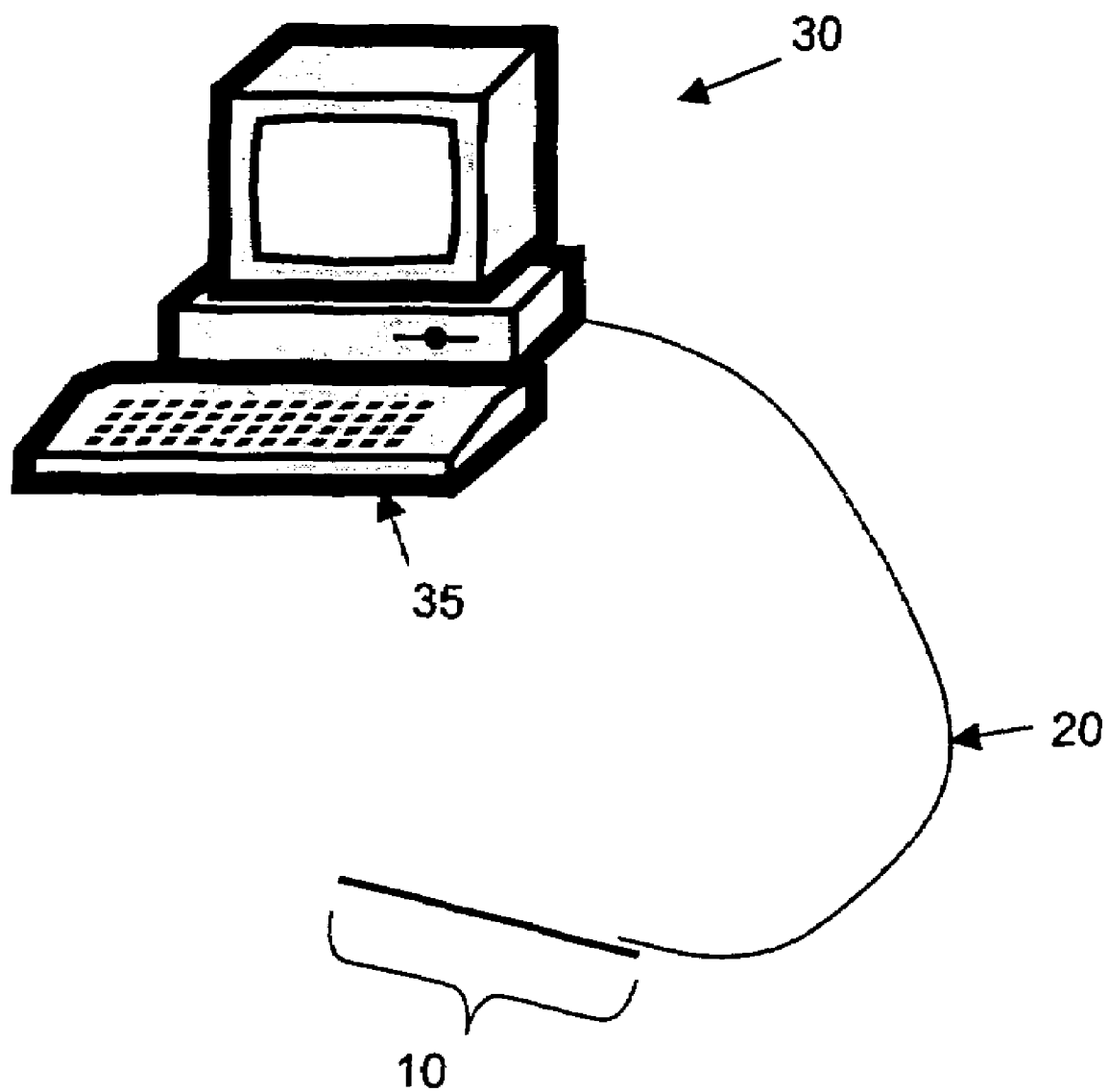
FIG. 5 is a block diagram of an exemplary ultrasound imaging system usable with various embodiments of the present invention.

An exemplary ultrasound imaging system usable with various embodiments of the present invention is shown in the block diagram of FIG. 5. The exemplary ultrasound imaging system includes a workstation 30, having an interface 35 (e.g., a keyboard, mouse, touchscreen display, etc.), a controller, and a display. The workstation 30 is coupled to an ultrasound probe 10 via a percutaneous catheter 20. The controller may be a computer, such as a personal computer, an internal microprocessor, or an application specific integrated circuit (ASIC) operating software that causes the controller to perform the control functions described herein. In this regard, the controller is preferably programmable so as to perform various processes and method steps described in greater detail below. Other configurations are also contemplated, and the system may or may not include further components as would be readily apparent to one of ordinary skill in the art after reading this disclosure.

Figure 1:
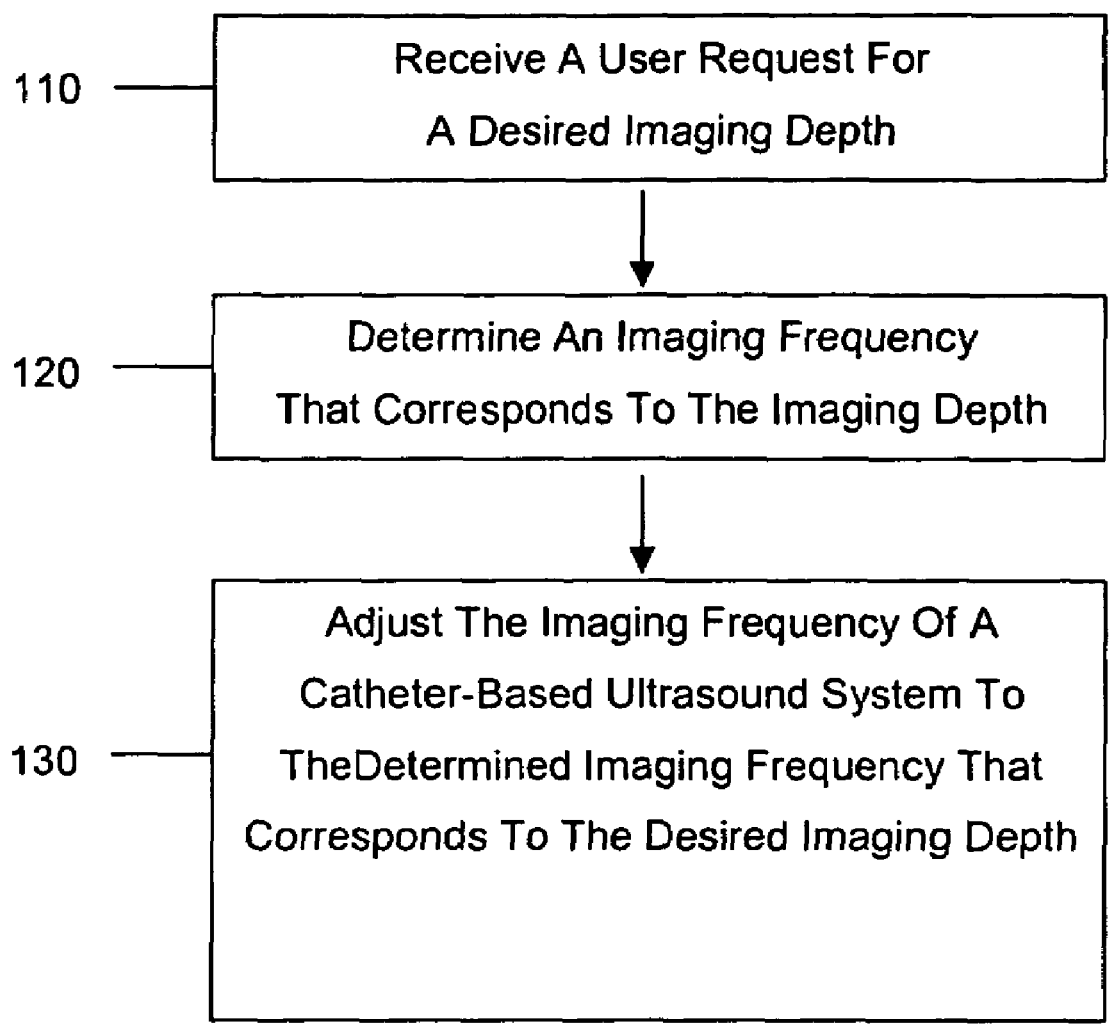
FIG. 1 is a flowchart of a method of controlling an ultrasound imaging system according to an embodiment of the present invention.

A method of controlling an ultrasound imaging system according to a first embodiment of the present invention is shown in the flowchart of FIG. 1. Specifically, in step 110, the ultrasound imaging system receives a user request for a desired imaging depth. By way of example, a user may: (1) enter a desired imaging depth (e.g., 5 cm) into a keyboard type interface, such as or including keys, buttons, toggle switches, rotary knobs, or various keypads, for example; (2) select an increase or decrease (i.e., a change) in a present imaging depth on a touchscreen display type interface; (3) issue a voice command to increase or decrease the present imaging depth interpreted by a voice recognition type interface; (4) select one of a list of possible imaging depths listed on a display using a mouse type interface; or (5) select any imaged feature or position on a video display showing the real-time image received from the ultrasound imaging system, such as by touching a touch-screen display or using a pixel-detecting pen coupled to the system to indicate the depth (and/or feature) for which optimized imaging is desired. In the embodiment that includes option (5), the imaging distance can be automatically calculated based upon the distance from the imager to the indicated point on the display. Other techniques for receiving a user request are also contemplated.

After the user request has been received in step 110, the ultrasound imaging system then automatically determines an imaging frequency that is calculated or known to correspond to the desired imaging depth in step 120. Step 120 may include processes such as retrieving a corresponding frequency from an electronic lookup table or database based upon the desired depth, or calculating a corresponding frequency using any one of a number of algorithms as would be readily apparent to one of ordinary skill in the art after reading this disclosure. The attenuations of sound in various tissues, including in blood, as a function of frequency have been measured and therefore are known and can be reduced to a look up table. Alternatively, the measured attenuation of sound in blood may be transformed into a computational algorithm, such as by a curve fit, that the imaging system can perform using the indicated imaging depth as an input. For example, the imaging depth of an ultrasound imager due to attenuation of sound in blood is an approximately linear gradient (classically expressed in dB/cm/MHz), such that the imaging depth at 4.5 MHz is about 11 cm and the imaging depth at 7.0 MHz is about 6 cm. Step 120 may be based on assumed physical properties or may include measuring physical properties of the fluids and/or tissues between the ultrasound sensor and the desired depth using data obtained from the ultrasound sensor or other sensors. In an embodiment, the look up table or algorithm may include attenuation effects of tissues, such as heart muscle or connective tissue in addition to blood.

In step 130, the medical imaging system then adjusts the imaging frequency of the system to the imaging frequency determined in step 120. In this manner, the medical imaging system automatically adjusts the imaging frequency in accordance with manual adjustment of the desired imaging depth. By automatically adjusting the imaging frequency, the medical imaging system can optimize the imaging frequency to match the desired imaging depth without requiring any further user interaction than the request for the desired imaging depth. As such, user interaction is minimized and the most optimized image is generated.

In an embodiment, the imaging system may also automatically adjust the time-gain compensation (up or down) in conjunction with adjusting the imaging frequency. The time-gain compensation also compensates for the attenuation of sound by blood or tissues. Since the time at which an echo signal is received is directly related to the distance the associated sound traveled (i.e., to and from the echoing structure), sound attenuation can be compensated for by amplifying the echo signals by an increasing amount based upon the time after the transmission pulse that the echo signal is received. The time-gain compensation may be adjusted according to an algorithm (such as a linear adjustment). However, applying too high a level of amplification in order to capture distant echo signals may result in greater noise in the image. Also, the appropriate time-gain may vary with imaging frequency. In this embodiment, when the imaging system receives a request for a new imaging depth, the system automatically adjusts the time-gain compensation to provide appropriate signal gain at the approximate time echo signals from that distance will be received at the ultrasound transducers.

According to an embodiment of the present invention, the catheter-based ultrasound probe includes an array of ultrasound transducers for generating ultrasound pulse(s), the array of ultrasound transducers, such that the system has an imaging frequency range of about 2 MHz to about 20 MHz. Preferably, the system is adjustable from about 2 MHz to about 20 MHz in about 0.5 MHz intervals. In this manner, the medical imaging system may adjust the imaging frequency to an imaging frequency selected from the group consisting essentially of 2.0 MHz, 2.5 MHz, 3.0 MHz . . . 19.0 MHz, 19.5 MHz, 20.0 MHz. In an embodiment, the increment of imaging frequency is more or less than about 0.5 MHz intervals. In an embodiment, the increment of imaging frequency is about 0.1 MHz. It should be appreciated, however, that the disclosed frequency range and adjustment increment may change as improvements in ultrasound imaging equipment become available, and/or to implement various embodiments of the present invention on non-ultrasound based medical imaging technology. Thus, the ranges noted above are not intended to be limiting.

Figure 2:
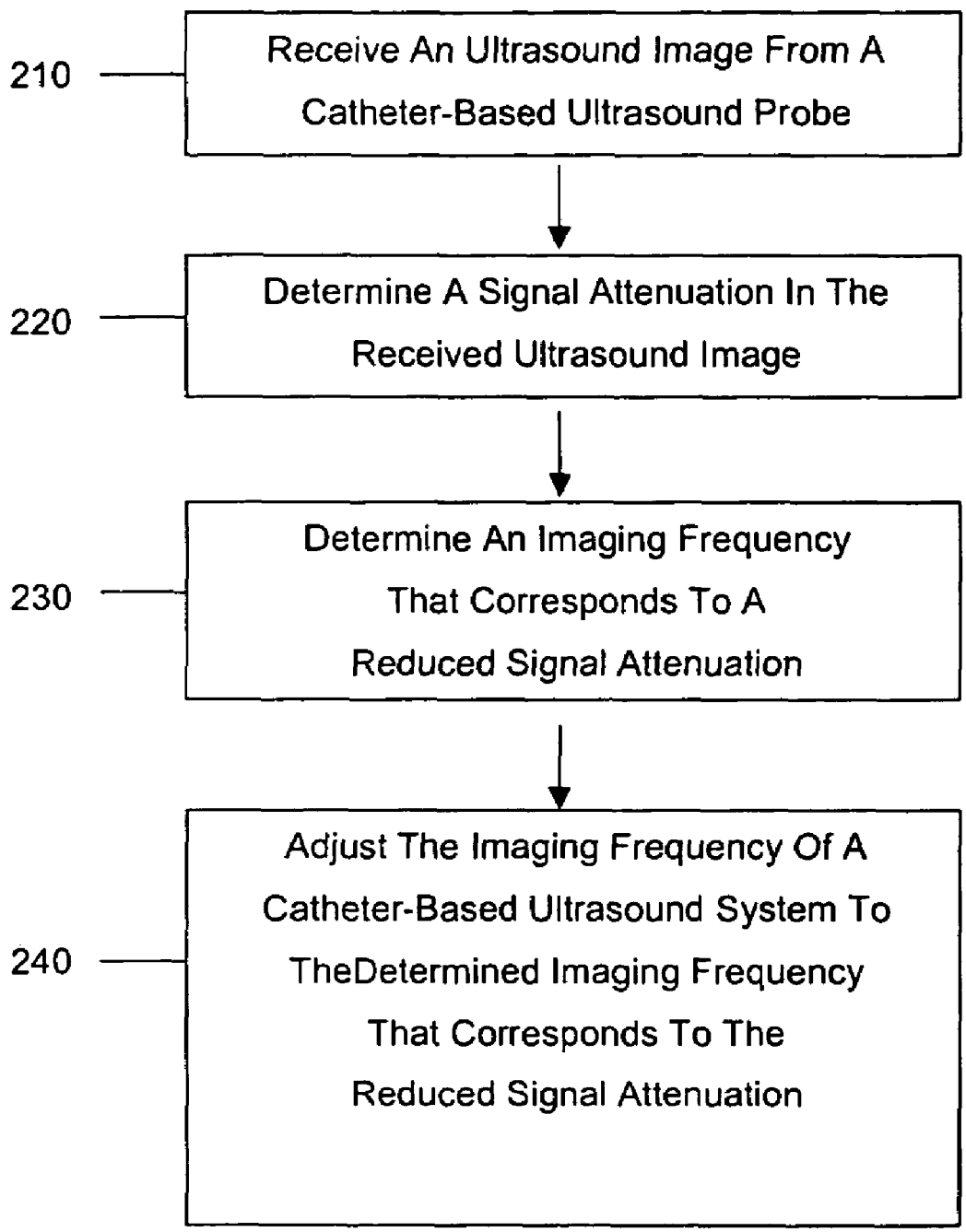
FIG. 2 is a flowchart of a method of compensating for signal attenuation in an ultrasound imaging system according to an embodiment of the present invention.

According to another embodiment of the present invention as shown in FIG. 2, the medical imaging system may further be provided with signal attenuation compensation capabilities. Signal attenuation generally refers to a reduction in signal quality, which may be caused by ultrasound pulses passing through different body tissues, structures, and fluids, such as for example calcification layers that absorb or scatter ultrasound energy. The resulting reduction in reflected ultrasound energy may result in degradation of the received echo signal quality. Such reduction in reflected ultrasound echo energy, and thus image signal quality may be compensated for by increasing or decreasing the imaging frequency from the frequency that typically provides an optimized image of a given imaging depth. Thus, the imaging frequency determined in step 120 may be further adjusted upon or after being implemented in step 130 to compensate for signal attenuation.

As shown in FIG. 2, an ultrasound image is received from the catheter-based ultrasound probe in step 210. The medical imaging system then, in step 220, determines a signal attenuation in the received ultrasound image. In step 220, the system may compare the measured received echo energy to the energy that would be expected if the attenuation matched expected values for the imaging depth. If the received energy is less than the expected energy, attenuation over the path length may be greater than the prediction or assumption. Similarly, if the received energy exceeds the expected energy, the actual attenuation may be less than the prediction or assumption. Attenuation may also be calculated using other methods, including an electronic table look up using the received or measured path length as an input, or an algorithm, such as a linear gradient, using the received or measured path length as an independent variable.

Once the signal attenuation has been determined in step 220, the medical imaging system then automatically determines an imaging frequency that corresponds to a reduced signal attenuation in step 230. By way of example, if the measured signal attenuation indicates less signal strength than expected (i.e., attenuation is greater than expected), such as due to the ultrasound pulse passing through a calcification layer, the determined imaging frequency may be an imaging frequency one (or more) increments (e.g., about 0.5 MHz or about 0.1 MHz, according to various embodiments) below (i.e., a lower frequency) that determined in step 120. If measured signal attenuation is less than expected, the imaging frequency may be increased in order to provide finer resolution of features at the selected imaging depth.

The medical imaging system then adjusts the imaging frequency of the system in step 240 to the determined imaging frequency that corresponds to the measured signal attenuation. According to an embodiment of the present invention, the medical imaging system may then verify that the change has improved the signal attenuation condition by re-running steps 220, 230, 240. In this manner, the medical imaging system may automatically re-adjust for signal attenuation with minimal user interaction required. According to an embodiment, the imaging system may also automatically adjust time-gain compensation in response to measured signal attenuation, such as by adjusting the slope of a linear algorithm (e.g., increasing or decreasing gain G where time-gain compensation for a given point in the image=G*t+C, where t corresponds to the time corresponding to the point of interest and C is a constant).

Figure 3:
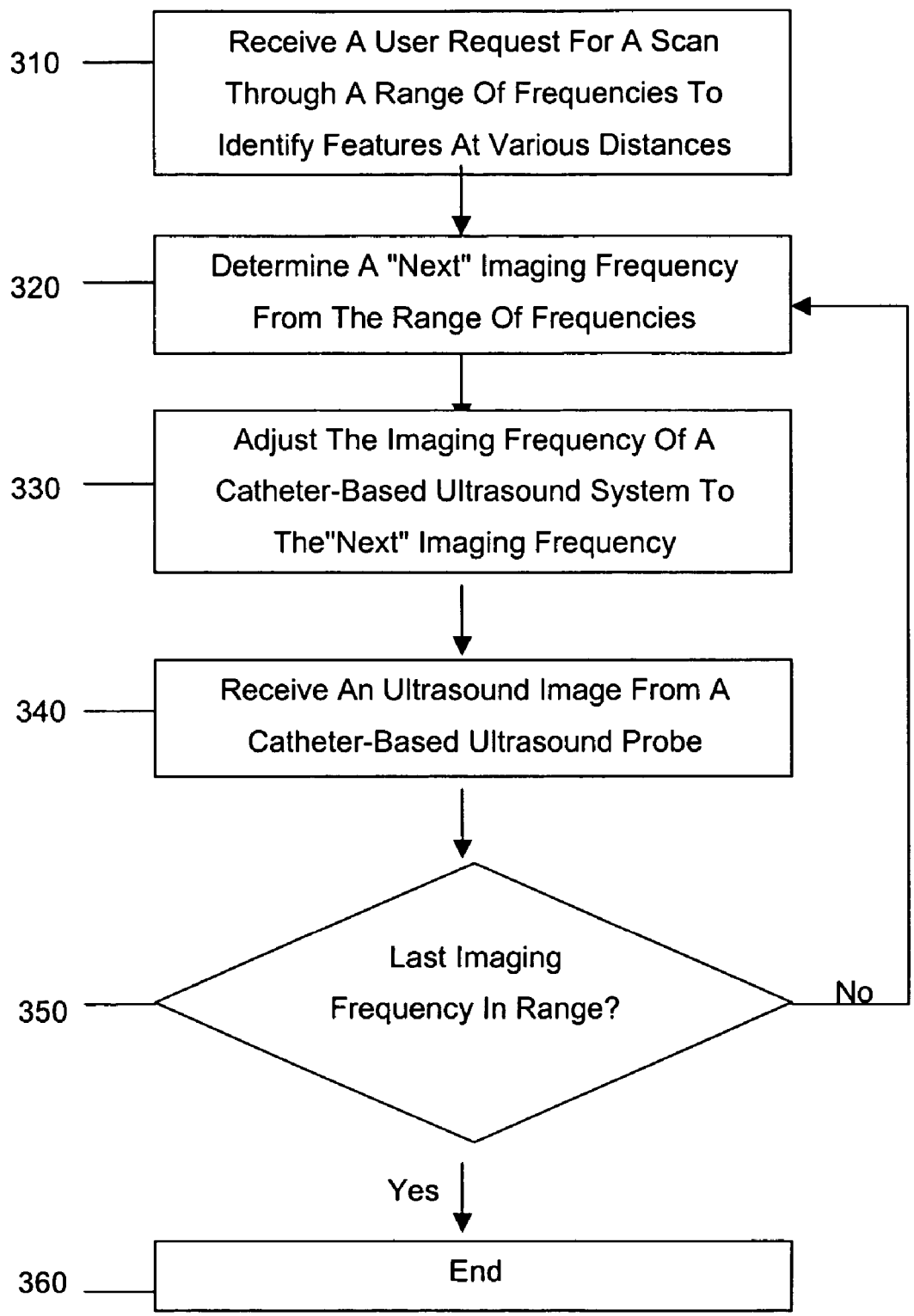
FIG. 3 is a flowchart of a method of auto-scanning a plurality of imaging frequencies in an ultrasound imaging system according to an embodiment of the present invention.

According to another embodiment of the present invention as shown in FIG. 3, the medical imaging system may be provided with a frequency scanning capability. More specifically, in step 310 the medical imaging system receives a user request for a scan through a range of frequencies to identify features at various distances, features including any number of viewable structures such as tissue masses, anomalies, etc. In step 320 the medical imaging system determines a "next" imaging frequency from the range of available frequencies. By way of example, if the scan is operating at its first cycle, the "next" imaging frequency may be the first available imaging frequency (e.g., 2.0 MHz for the medical imaging system previously discussed or the current imaging frequency+/−the delta frequency). The medical imaging system then adjusts the imaging frequency in step 330 to the frequency determined in step 320. After an ultrasound image from the catheter-based ultrasound probe is received in step 340, the medical imaging system then determines whether the frequency determined in step 320 is the last imaging frequency in the range of available frequencies. If not, the medical imaging system re-runs step 320, else the process ends in step 360. Alternatively, steps 310 through 350 may be performed until stopped by the operator.

Figure 4:
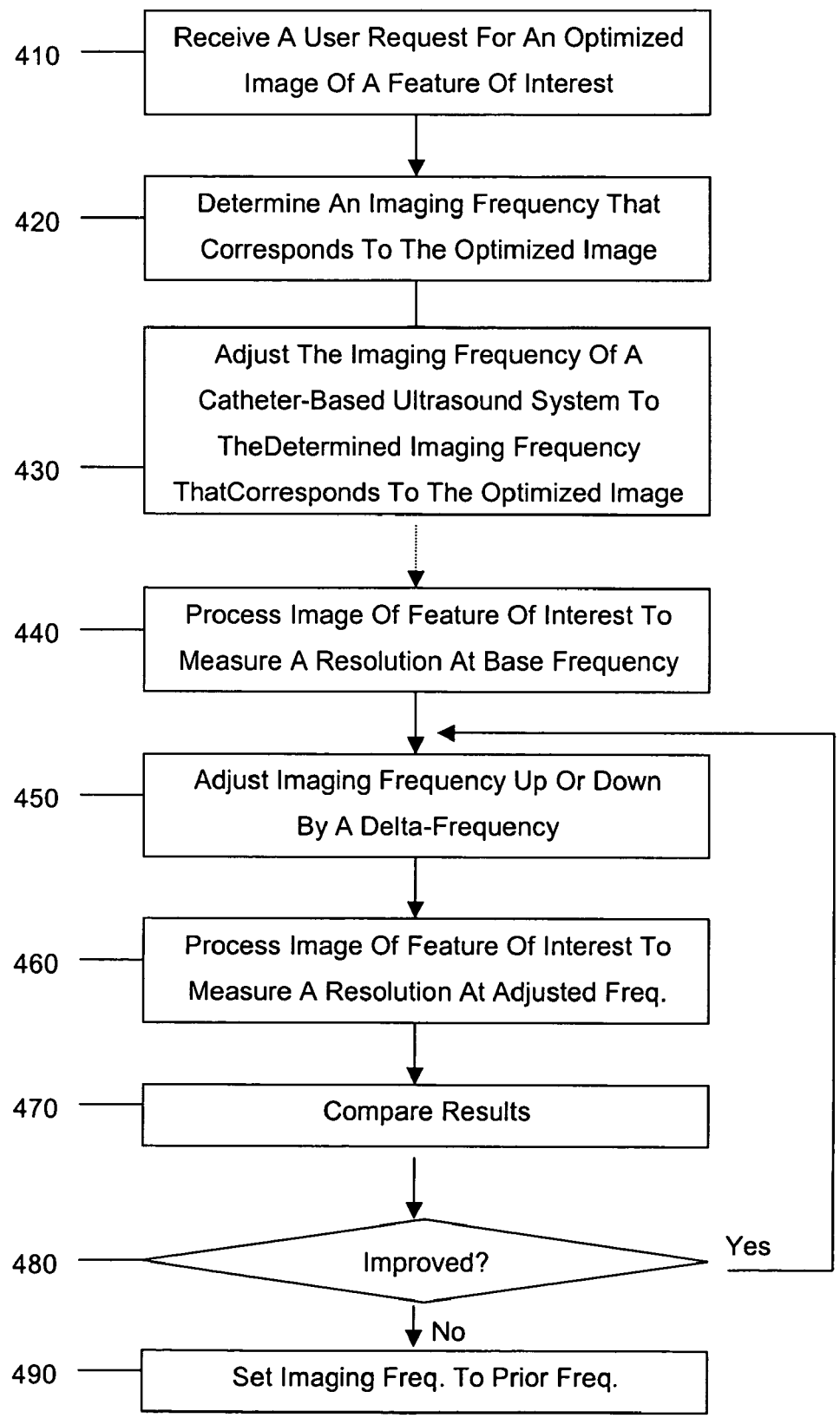
FIG. 4 is a flowchart of a method of optimizing an image in an ultrasound imaging system according to an embodiment of the present invention.

According to another embodiment of the present invention, the medical imaging system may be provided with an optimization feature as shown in FIG. 4. In particular, in step 410 the medical imaging system receives a user request for an optimized image of a feature of interest, indicated by the point of focus set by the user, or assumed by default to be at 75% of the imaging depth. As an example, once the scanning process shown in FIG. 3 has completed, a user may desire an optimized image of one of the features discovered during the scan and presented on the ultrasound image display. Alternatively, an "auto-recognize" feature may be provided that automatically recognizes features and initiates the request received in step 410.

Referring to FIG. 4, the medical imaging system in step 420 determines an imaging frequency that corresponds to the optimized image based on the measured depth to the feature. The determination of an imaging frequency may assume physical properties for intervening tissues, including in an embodiment, assuming properties based upon detected intervening structures and fluids and measured parameters (e.g., continuity of imaged tissue, received echo signal strength, etc.). Alternatively, using the scan of FIG. 3 as an example of a starting point, if a feature becomes apparent at about 4.0 MHz during the frequency scan, the medical imaging system may select 4.0 MHz in step 420.

In step 430 the medical imaging system then adjusts the imaging frequency to the frequency determined in step 420. This may be followed by a confirmation step that queries the user whether the image has been sufficiently optimized. If the user responds that further optimization is required, then the process shown in FIG. 4 may repeat (even with a smaller delta frequency).

In an another embodiment illustrated in FIG. 4, the medical imaging system may include an image recognition and processing capability that assists in the optimization process. Specifically, following step 430, the image processing capability determines a measure of the image quality of the feature selected for imaging, such as by calculating a measure of resolution by measuring the definition of a boundary. For example, the image processing capability may determine the range over which echoes from a surface are received along a vector, which may be combined with statistical measures of the changes in intensity along the vector in the vicinity of the structure.

After an image quality (e.g., resolution) measure has been obtained for an initial frequency ($F_0$), the medical imaging system adjusts the imaging frequency of the catheter-based ultrasound probe in step 450 to a higher or lower frequency ($F_1$) and obtains another image. In step 450, the frequency may be adjusted up or down as determined by the imaging processing system as necessary to determine if optimum image quality (e.g., resolution) is achieved. By way of example, the subsequent discussion assumes step 450 increases frequency the first time through the process (default), but the process may be implemented by decreasing the frequency the first time through. In applications where moving tissues, such as muscles and structures of the heart, are imaged, the second image may need to be taken (timed or triggered) so as to correspond to a similar configuration as in the first image so that image quality measurements can be compared. In a particular embodiment suitable for use in intracardiac imaging, the first and second images are timed or initiated based upon an input (e.g., an ECG signal) to occur at the same point in the cardiac cycle. By acquiring the second image at or nearly at the same point in the cardiac cycle as the first image, measures of image quality in the two images may be compared because the same structure will appear at approximately the same position (e.g., imaging depth) in both images.

In step 460, the image obtained at the new frequency $F_1$ is processed to determine a measure of the image quality (e.g., resolution) of the feature selected for imaging. Then, in step 470, the two measures of resolution for images taken at $F_0$ and $F_1$ are compared to determine if the image quality (e.g., resolution) is improved or degraded as a result of the change in imaging frequency.

In step 480, the medical imaging system determines whether to further adjust the frequency or whether an optimum frequency was obtained. If there is an improvement in image quality (e.g., resolution) when the imaging frequency is increased from $F_0$ to $F_1$, then the process returns to step 450, sequentially increasing (or decreasing) the frequency to new frequency $F_i$ and comparing the resulting image quality (e.g., resolution) measurements. Steps 450 through 480 are repeated until the system determines there is no change or a degradation in image quality (e.g., resolution) when frequency is increased from $F_{i-1}$ to $F_i$. When that determination is made, the medical imaging system sets the imaging frequency to the frequency that provided the best measure of image quality (e.g., $F_{i-1}$) in step 490.

If the first comparison of the measures of image quality (e.g., resolution) in steps 470 determines that the resolution is unchanged or degraded by increasing the frequency from $F_0$ to $F_1$, then in step 480 the medical imaging system determines that the optimum frequency may be lower than the initial frequency ($F_0$). In that case, the process returns to step 450 where the imaging frequency is decreased to $F_1$. Then steps 460 through 480 are performed to determine if lowering the imaging frequency improved the image quality (e.g., resolution) of the desired feature. Steps 450 through 480 are repeated until the system determines there is no change or a degradation in image quality when frequency is decreased from $F_{i-1}$ to $F_i$. When that determination is made, the medical imaging system sets the imaging frequency to the frequency that provided the best measure of image quality (e.g., $F_{i-1}$) in step 490.

As set forth in the aforementioned embodiments, medical imaging systems have been disclosed with autofrequency selection that provide a user with relatively simple and efficient operations of a given medical imaging system. Additional features such as frequency scanning, signal attenuation compensation, and image optimization may be utilized as desired. Further, a medical imaging system according to the present invention may merge or correlate ultrasound images with other medical information, including concurrent instrumentation data, such as electrocardiogram (ECG) data. For example, in medical procedures in which the imaging system is used to image portions of a patient's heart, intracardiac electrophysiology catheters may also be present in the heart. In such procedures, displaying ECG data (such as a trace moving across the screen) on the same monitor that displays ultrasound images would aid the physician. Such ECG data may be correlated to the ultrasound images so the current ECG trace(s) is displayed along with the current ultrasound image. The ECG data may be further correlated to the image so the display shows only the ECG trace of the ECG catheter that is presently imaged by imaging system.

The foregoing description of various embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments and with various modifications as are suited to the particular use contemplated.

What is claimed is:

1. An ultrasound imaging system, comprising:
   an interface for receiving user input;
   a controller coupled to the interface, the controller being adapted and configured to adjust parameters for a catheter-based ultrasound probe in response to received user input; and
   a catheter-based ultrasound probe coupled to the controller,
   wherein the controller is programmed to:
      receive a user request for a desired imaging depth;
      automatically determine an imaging frequency that corresponds to the desired imaging depth;
      adjust the frequency of signals applied to the catheter-based ultrasound probe to the determined imaging frequency that corresponds to the desired imaging depth;
      automatically process a first image of a feature of interest imaged at the determined imagine frequency to measure image resolution;
      adjust the frequency of signals applied to the catheter-based ultrasound probe by a delta-frequency;
      automatically process a second image of the feature of interest imaged at the delta-frequency adjusted imagining frequency to measure image resolution;
      automatically compare the measured resolution of the first image to the measured resolution of the second image; and
      automatically adjust the frequency of signals applied to the catheter-based ultrasound probe to the adjusted imaging frequency if the measured resolution of the second image is better than the measured resolution of the first image.

2. The ultrasound imaging system of claim 1, wherein the determined imaging frequency is selected from a range of incremented frequencies separated by increments of about 0.5 MHz.

3. The ultrasound imaging system of claim 1, wherein the determined imaging frequency is selected from a range of incremented frequencies separated by increments of about 0.1 MHz.

4. The ultrasound imaging system of claim 1, wherein the determined imaging frequency is within a range of about 2 MHz to about 20 MHz.

5. The ultrasound imaging system of claim 1, wherein receiving a user request for a desired imaging depth comprises receiving a user request for a change in a present imaging depth.

6. The ultrasound imaging system of claim 1, wherein receiving a user request for a desired imaging depth comprises receiving a user request for a scan through a range of frequencies.

7. The ultrasound imaging system of claim 6, wherein determining an imaging frequency for the catheter-based ultrasound probe that corresponds too the desired imaging depth comprises progressively determining a next imaging frequency for the scan through the range of frequencies.

8. The ultrasound imaging system of claim 1,
wherein receiving a user request for a desired imaging depth comprises receiving user designation of a feature within an image,
wherein automatically determining an imaging frequency that corresponds to the desired imaging depth comprises automatically determining an imaging frequency that corresponds to the user designated feature, and
wherein adjusting the frequency of signals applied to the catheter-based ultrasound probe comprises automatically adjusting the frequency of signals applied to the catheter-based ultrasound probe to the determined imaging frequency that corresponds to the user designated feature.

9. The ultrasound imaging system of claim 1, wherein the controller is further programmed to:
automatically adjust the frequency of signals applied to the catheter-based ultrasound probe to the determined imaging frequency if the measured resolution of the first image is better than the measured resolution of the second image.

10. An ultrasound imaging system, comprising:
an interface for receiving user input;
a controller coupled to the interface, the controller being adapted and configured to adjust parameters for a catheter-based ultrasound probe in response to received user input; and
a catheter-based ultrasound probe coupled to the controller,
wherein the controller is programmed to:
receive a user request for a desired imagine depth;
automatically determine an imaging frequency that corresponds to the desired imaging depth;
adjust the frequency of signals applied to the catheter-based ultrasound probe to the determined imaging frequency that corresponds to the desired imaging depth;
receive a signal from an electrocardiogram and correlate the signal with the received ultrasound image;
acquire a first image at a point in a cardiac cycle based on signals received from the electrocardiogram;
automatically process the first image of a feature of interest imaged at the determined imaging frequency to measure image resolution;
adjust the frequency of signals applied to the catheter-based ultrasound probe by a delta-frequency;
acquire a second image at approximately the same point in the cardiac cycle as the first image based on signals received from the electrocardiogram;
automatically process the second image of the feature of interest imaged at the delta-frequency adjusted imaging frequency to measure image resolution;
compare the measured resolution of the first image to the measured resolution of the second image;
automatically adjust the frequency of signals applied to the catheter-based ultrasound probe to the determined imaging frequency if the measured resolution of the first image is better than the measured resolution of the second image; and
automatically adjust the frequency of signals applied to the catheter-based ultrasound probe to the adjusted imaging frequency if the measured resolution of the second image is better than the measured resolution of the first image.

11. A method of controlling an ultrasound imaging system including a catheter-based ultrasound probe, comprising:
receiving a user request for a desired imaging depth;
automatically determining an imaging frequency that corresponds to the desired imaging depth;
adjusting the frequency of signals applied to the catheter-based ultrasound probe to the determined imaging frequency that corresponds to the desired imaging depth;
automatically processing a first image of a feature of interest imaged at the determined imaging frequency to measure image resolution;
adjusting the frequency of signals applied to the catheter-based ultrasound probe by a delta-frequency;
automatically processing a second image of a feature of interest imaged at the delta-frequency adjusted imaging frequency to measure image resolution;
automatically comparing the measured resolution of the first image to the measured resolution of the second image; and
automatically adjusting the frequency of signals applied to the catheter-based ultrasound probe to the adjusted imaging frequency if the measured resolution of the second image is better than the measured resolution of the first image.

12. The method of claim 11, wherein the determined imaging frequency is selected from a range of incremented frequencies separated by increments of about 0.5 MHz.

13. The method of claim 11, wherein the determined imaging frequency is selected from a range of incremented frequencies separated by increments of about 0.1 MHz.

14. The method of claim 11, wherein the determined imaging frequency is within a range of about 2 MHz to about 20 MHz.

15. The method of claim 11, wherein receiving a user request for a desired imaging depth comprises receiving a user request for a change in the present imaging depth.

16. The method of claim 11, wherein receiving a user request for a desired imaging depth comprises receiving a user request for a scan through a range of frequencies to identify features at various depths.

17. The method of claim 16, wherein determining an imaging frequency for the catheter-based ultrasound probe that corresponds to the desired imaging depth comprises progressively determining a next imaging frequency for the scan through the range of frequencies.

18. The method of claim 11,
wherein receiving a user request for a desired imaging depth comprises receiving user designation of a feature within an image, wherein determining an imaging frequency that corresponds to the desired imaging depth comprises automatically determining an imaging frequency that corresponds to a distance from a transducer to the user designated feature, and wherein adjusting the frequency of signals applied to the catheter-based ultrasound probe comprises automatically adjusting the frequency of signals applied to the catheter-based ultrasound probe to the determined imaging frequency that corresponds to the user designated feature.

19. The method of claim 11, further comprising:

automatically adjusting the frequency of signals applied to the catheter-based ultrasound probe to the determined imaging frequency if the measured resolution of the first image is better than the measured resolution of the second image.

20. An ultrasound imaging system, comprising:

a catheter-based ultrasound probe, means for receiving a user request for a desired imaging depth;

means for automatically determining an imaging frequency that corresponds to the desired imaging depth;

means for adjusting the frequency of signals applied to the catheter-based ultrasound probe to the determined imaging frequency that corresponds to the desired imaging depth;

means for receiving a signal from an electrocardiogram and correlating the signal with ultrasound images received from the catheter-based ultrasound probe;

means for acquiring a first image at a point in a cardiac cycle based on signals received from the electrocardiogram;

means for automatically measuring image resolution of the first image of a feature of interest imaged at the determined imaging frequency;

means for adjusting the frequency of signals applied to the catheter-based ultrasound probe by a delta-frequency;

means for acquiring a second image at approximately the same point in the cardiac cycle as the first image based on signals received from the electrocardiogram;

means for automatically measuring image resolution of the second image of the feature of interest imaged at the delta-frequency adjusted imaging frequency;

means for comparing the measured resolution of the first image to the measured resolution of the second image; and means for automatically adjusting the frequency of signals applied to the catheter-based ultrasound probe to the adjusted imaging frequency if the measured resolution of the second image is better than the measured resolution of the first image.

21. The ultrasound imaging system of claim 20, further comprising:

means for automatically adjusting the frequency of signals applied to the catheter-based ultrasound probe to the determined imaging frequency if the measured resolution of the first image is better than the measured resolution of the second image.

22. A method of controlling an ultrasound imaging system including a catheter-based ultrasound probe, comprising:

receiving a user request for a desired imaging depth;

automatically determining an imaging frequency that corresponds to the desired imaging depth;

adjusting the frequency of signals applied to the catheter-based ultrasound probe to the determined imaging frequency that corresponds to the desired imaging depth;

receiving a signal from an electrocardiogram and correlate the signal with the received ultrasound image;

acquiring a first image at a point in a cardiac cycle based on signals received from the electrocardiogram;

automatically processing the first image of a feature of interest imaged at the determined imaging frequency to measure image resolution;

adjusting the frequency of signals applied to the catheter-based ultrasound probe by a delta-frequency;

acquiring a second image at approximately the same point in the cardiac cycle as the first image based on signals received from the electrocardiogram;

automatically processing the second image of the feature of interest imaged at the delta-frequency adjusted imaging frequency to measure image resolution;

comparing the measured resolution of the first image to the measured resolution of the second image;

automatically adjusting the frequency of signals applied to the catheter-based ultrasound probe to the determined imaging frequency if the measured resolution of the first image is better than the measured resolution of the second image; and automatically adjusting the frequency of signals applied to the catheter-based ultrasound probe to the adjusted imaging frequency if the measured resolution of the second image is better than the measured resolution of the first image.

* * * * *

UNITED STATES PATENT AND TRADEMARK OFFICE
CERTIFICATE OF CORRECTION

PATENT NO. : 7,654,958 B2
APPLICATION NO. : 10/827520
DATED : February 2, 2010
INVENTOR(S) : Charles Bryan Byrd et al.

It is certified that error appears in the above-identified patent and that said Letters Patent is hereby corrected as shown below:

Column 8, claim 1, line 48, kindly delete "imagine" and replace with --imaging--.

Column 9, claim 7, line 18, kindly delete "too" and replace with --to--.

Column 9, claim 10, line 52, kindly delete "imagine" and replace with --imaging--.

Signed and Sealed this
Twenty-sixth Day of February, 2013

Teresa Stanek Rea
*Acting Director of the United States Patent and Trademark Office*